United States Patent
Fields et al.

(10) Patent No.: US 8,351,894 B2
(45) Date of Patent: Jan. 8, 2013

(54) MOBILE WIRELESS COMMUNICATIONS DEVICE WITH ORIENTATION SENSING AND RELATED METHODS

(75) Inventors: Greg Fields, Waterloo (CA); David Dougall, Waterloo (CA)

(73) Assignee: Research In Motion Limited, Waterloo, Ontario (CA)

( * ) Notice: Subject to any disclaimer, the term of this patent is extended or adjusted under 35 U.S.C. 154(b) by 496 days.

(21) Appl. No.: 12/394,370

(22) Filed: Feb. 27, 2009

(65) Prior Publication Data
US 2010/0222099 A1    Sep. 2, 2010

(51) Int. Cl.
*H04M 1/00* (2006.01)
(52) U.S. Cl. .................. 455/404.1; 455/556.1; 455/567
(58) Field of Classification Search .............. 455/404.1, 455/556.1, 567; 340/573.1
See application file for complete search history.

(56) References Cited

U.S. PATENT DOCUMENTS

| | | | |
|---|---|---|---|
| 6,611,783 B2 | 8/2003 | Kelly et al. .................. 702/105 |
| 7,787,857 B2 * | 8/2010 | Peterman ................... 455/404.1 |
| 2001/0020898 A1 | 9/2001 | Pierce et al. | |
| 2004/0214594 A1 * | 10/2004 | Holman, IV ............... 455/550.1 |
| 2005/0240253 A1 | 10/2005 | Tyler et al. | |
| 2006/0161218 A1 | 7/2006 | Danilov | |
| 2006/0241718 A1 | 10/2006 | Tyler et al. | |
| 2007/0250119 A1 | 10/2007 | Tyler et al. | |
| 2008/0009772 A1 | 1/2008 | Tyler et al. | |
| 2008/0228239 A1 | 9/2008 | Tyler et al. | |
| 2009/0216156 A1 * | 8/2009 | Lengsfeld et al. ............ 600/595 |
| 2009/0298533 A1 * | 12/2009 | Alameh et al. ............. 455/556.1 |
| 2009/0306741 A1 | 12/2009 | Hogle et al. | |
| 2009/0312808 A1 | 12/2009 | Tyler et al. | |
| 2009/0312817 A1 | 12/2009 | Hogle et al. | |
| 2009/0326604 A1 | 12/2009 | Tyler et al. | |

FOREIGN PATENT DOCUMENTS

| | | |
|---|---|---|
| JP | 2004038430 | 2/2004 |
| WO | 0143473 | 6/2001 |

OTHER PUBLICATIONS

Culhane et al., "Accelerometers in Rehabilitation Medicine for Older Adults", *Age and Aging 2005*, Oxford University Press, doi:10.1093/ageing/afi 192, 34:556-560.
Zhang et al., "Fall Detection by Embedding An Accelerometer In Cellphone And Using KFD Algorithm", *IJCSNS International Journal of Computer Science and Network Security*, vol. 6, No. 10, Oct. 2006, 277-284.
Neel Parikh, CS297 Report, "Accelerometer Based Motion Gestures for Mobile Devices", Department of Computer Science, San Jose State University, Spring 2008, 1-14.
BrainPort Technologies, Let us help you achieve balance, http://wicab.co.uk/index.php, downloaded Apr. 2012, p. 1.

(Continued)

*Primary Examiner* — Vibol Tan
(74) *Attorney, Agent, or Firm* — Allen, Dyer, Doppelt, Milbrath & Gilchrist, P.A.

(57) ABSTRACT

A mobile wireless communications device may include a housing, a wireless transceiver carried by the housing, and a display carried by the housing. The mobile wireless communications device may further include a non-visual indicator carried by the housing, and an orientation sensor carried by the housing. A controller may be carried by the housing, and coupled to the wireless transceiver and the display to perform at least one mobile wireless communications function. The controller may also be switchable to a stabilization mode to activate the non-visual indicator based upon the orientation sensor sensing relative angular movement beyond a threshold.

14 Claims, 6 Drawing Sheets

OTHER PUBLICATIONS

BrainPort Technologies, About Us, http://wicab.co.uk/about/, downloaded Apr. 2012, p. 1.
BrainPort Technologies, Our technology, http://wicab.co.uk/technology/, downloaded Apr. 2012, p. 1.
BrainPort Technologies, Results of completed studies, http://wicab.co.uk/research/, downloaded Apr. 2012, p. 1.
BrainPort Technologies, BrainPort Balance Device, http://wicab.co.uk/clinicians/, downloaded Apr. 2012, p. 1.

* cited by examiner

MOBILE WIRELESS COMMUNICATIONS DEVICE WITH ORIENTATION SENSING AND RELATED METHODS

TECHNICAL FIELD

The present disclosure relates to the field of wireless communications and, more particularly, to mobile wireless communications devices with sensors and related methods.

BACKGROUND

Some people live with disabilities as a result of a traumatic brain injury (TBI). As a result of a TBI, a person may suffer from a balance disturbance. A balance disturbance may cause a person to unknowingly fall, which may cause further injury. A person having a TBI and an increased risk of falling may have a decreased level of independence, and thus, varying amounts and types of supervision may be desired.

DETAILED DESCRIPTION OF THE EMBODIMENTS

The present description is made with reference to the accompanying drawings, in which various example embodiments are shown. However, many different example embodiments may be used, and thus the description should not be construed as limited to the example embodiments set forth herein. Rather, these example embodiments are provided so that this disclosure will be thorough and complete. Like numbers refer to like elements throughout.

Mobile communications devices have become an integral part of society over the last two decades. Indeed, more than eighty-two percent of Americans own a mobile communications device, for example, a cell phone device. Even further, international cell phone device penetration has reached 3.3 billion units. In other words, approximately half the world's population has a cell phone device. The typical cell phone device includes an antenna, and a transceiver coupled to the antenna. The transceiver and the antenna cooperate to transmit and receive communications signals with a network infrastructure, usually maintained by a cell phone provider.

Although the first cell phone devices typically included only voice or limited short message service capabilities, the capabilities of cell phone devices have increased greatly over the last decade. More so, the typical "smart phone," i.e. a cell phone device with advanced capabilities, rivals the processing power and memory of desktop personal computers of a decade earlier. For example, the typical smart phone is capable of running a variety of advanced programs spanning from typical word processing software to global positioning system navigation software.

As the capabilities of cell phone devices have increased, cell phone providers have gained access to new potential revenue streams. For example, cell phone providers sell multimedia content to their subscribers. More specifically, the cell phone providers typically sell ring tones and digital music files via the cell phone. The cell phone providers charge small fees for each transaction, which is separate from the typical monthly subscription fee.

Another recently developed potential revenue stream is the sale of third party applications for the cell phone devices. In other words, the cell phone providers provide a venue for third parties to sell their software to subscribers. Of course, the cell phone providers typically derive a fee from the third parties for providing the venue. A particularly advantageous venue for these third party applications is the so-called mobile application store platform. For example, the Application Center of Research In Motion Limited, the assignee of the present application, provides an on-device platform for third party applications. Because of the easy access to a plurality of third party applications and the capability of paying for such applications wirelessly via the cell phone subscriber's account, the mobile application store platform provides a robust consumer solution with great potential for large revenue.

A mobile wireless communications device may include a housing, a wireless transceiver carried by the housing, and a display carried by the housing. The mobile wireless communications device may further include a non-visual indicator carried by the housing, and an orientation sensor carried by the housing. A controller may be carried by the housing, and coupled to the wireless transceiver and the display to perform at least one mobile wireless communications function. The controller may also be switchable to a stabilization mode to activate the non-visual indicator based upon the orientation sensor sensing relative angular movement beyond a threshold. In other words, the stabilization mode may be selectively enabled to activate the non-visual indicator based upon the orientation sensor sensing relative angular movement beyond a threshold.

The mobile wireless communications device may also include an input device carried by the housing and cooperate with the controller to switch the controller to the stabilization mode. The input device may cooperate with the controller to set the threshold. The threshold may be less than or equal to 15 degrees from vertical, for example.

The controller may determine the relative angular movement relative to a baseline orientation. The input device may cooperate with the controller to set the baseline orientation, for example. The non-visual indicator may include a vibratory indicator. The non-visual indicator may also include an audible indicator. The orientation sensor may include an accelerometer. The mobile wireless communications device may include a memory coupled to the controller for storing the threshold.

Another aspect is directed to a method of upgrading a mobile wireless communications device that may include a housing, a wireless transceiver carried by the housing, and a display carried by the housing. The mobile wireless communications device may also include a non-visual indicator carried by the housing and an orientation sensor carried by the housing. A controller may also be carried by the housing and coupled to the wireless transceiver and the display to perform at least one communications function. The method may include configuring the controller to be switchable to a stabilization mode to activate the non-visual indicator based upon the orientation sensor sensing relative angular movement beyond a threshold to upgrade the mobile wireless communications device.

Figure 1A:
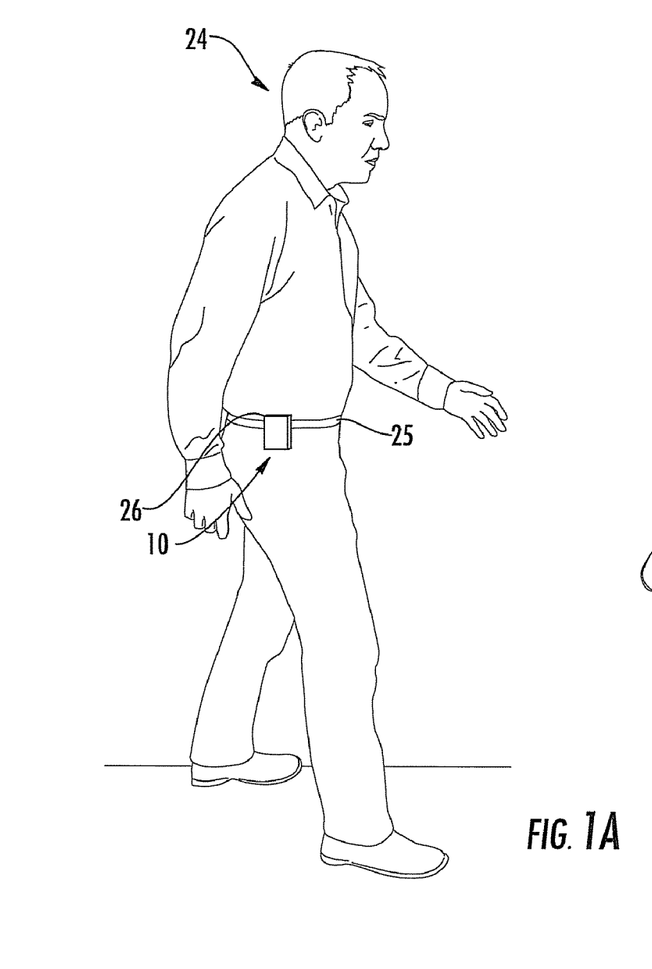
FIGS. 1a-1b are schematic diagrams of a mobile wireless communications device on a user at two different times, respectively, and according to an example embodiment of the present disclosure.
Figure 1B:
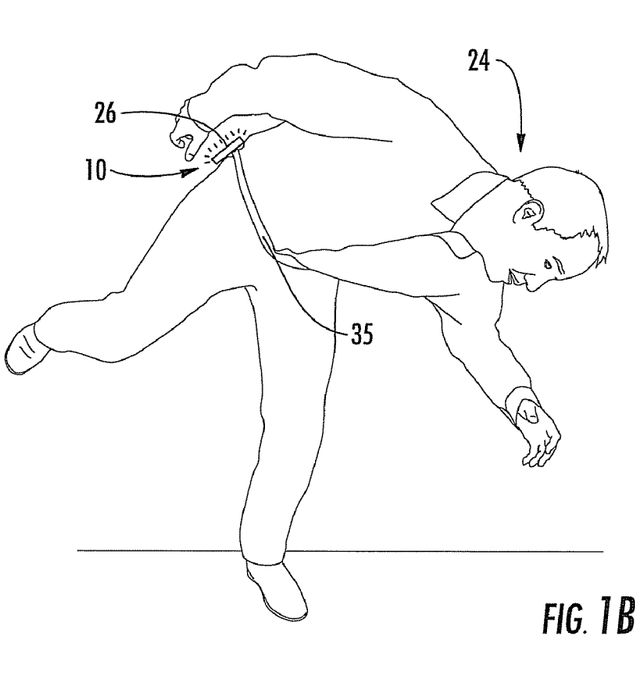

Referring initially to FIGS. 1a and 1b a user 24, for example that suffers from a TBI, is illustratively wearing a mobile wireless communications device 10 in a holster 26 on his belt 25. The mobile wireless communications device 10 is switched in a stabilization mode. In other words, the stabilization mode is selectively enabled. A user 24 that suffers from a TBI may have an increased chance of unknowingly falling. As illustrated in FIG. 1b, in the stabilization mode, the mobile wireless communications device 10 may alert the user 24 of an impending fall by activating a non-visual indicator, such as generating a vibrating alert. Alerting the user 24 of an impending fall may be particularly advantageous for reducing the number of falls, and thus improving the overall safety of the user, especially one that suffers from a TBI. Furthermore, notifying the user 24 of an impending fall prior to falling, may help condition the user 24 to not fall, and thus help rehabilitate users that suffer from TBI. Of course, as will be appreciated by those skilled in the art, the user 24 may not suffer from a TBI to benefit from the mobile wireless communications device 10 having the stabilization mode, as it may also be useful for other applications.

Figure 2:
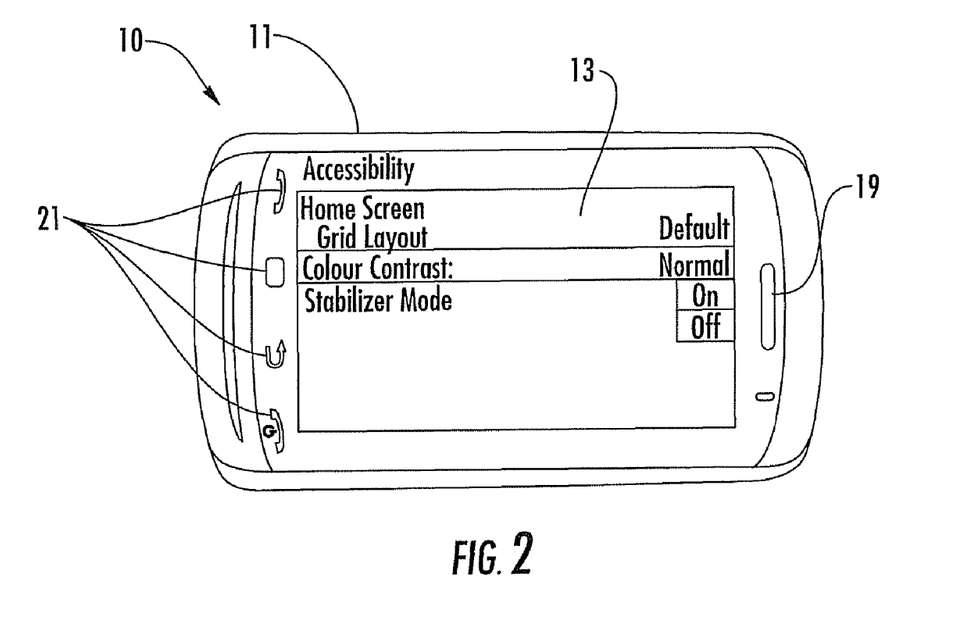
FIG. 2 is a plan view of the mobile wireless communications device shown in FIGS. 1a-1b illustrating a first menu, according to an example embodiment.
Figure 3:
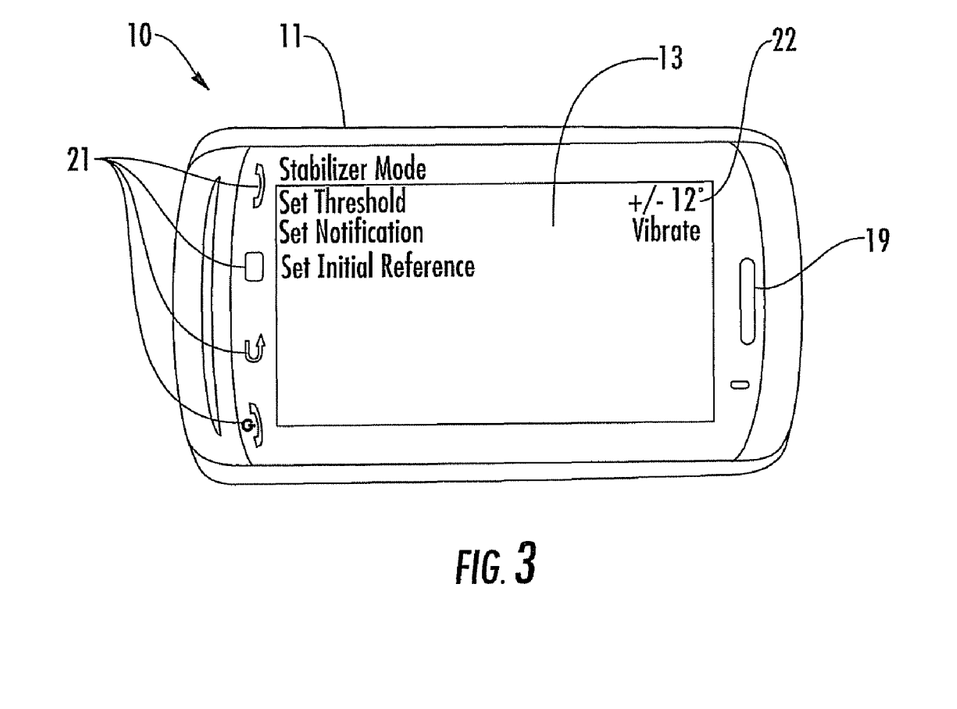
FIG. 3 is a plan view of the mobile wireless communications device shown in FIGS. 1a-1b illustrating a second menu, according to an example embodiment.
Figure 4:
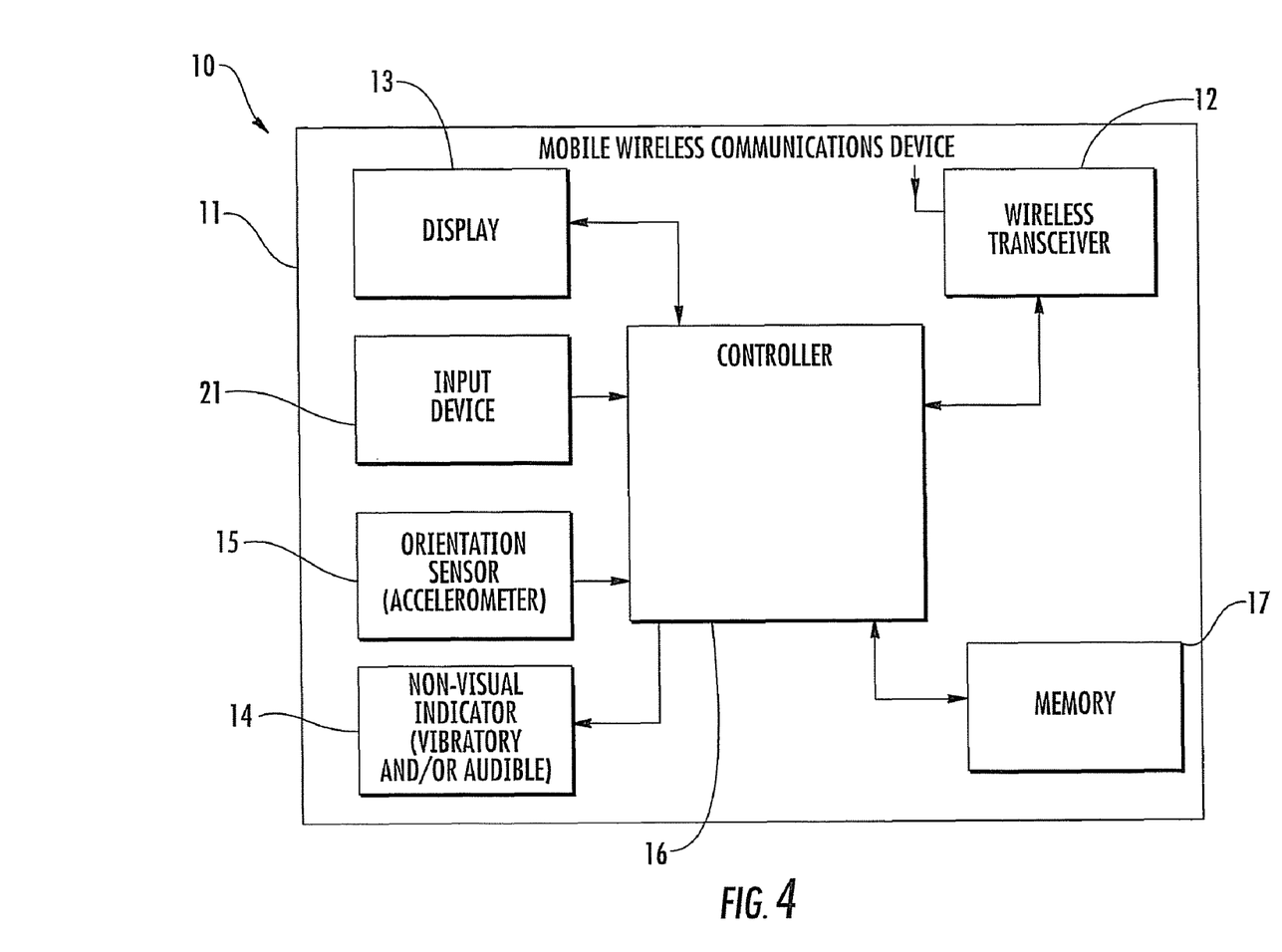
FIG. 4 is a schematic block diagram of the mobile wireless communications device of FIGS. 1a-1b, according to an example embodiment.

Referring now additionally to FIGS. 2-4, the mobile wireless communications device 10 is now described in greater detail. The mobile wireless communications device 10 illustratively includes a housing 11, a wireless transceiver 12 carried by the housing, a display 13 carried by the housing, and a non-visual indicator 14 carried by the housing. The mobile wireless communications device 10 also illustratively includes an orientation sensor 15 carried by the housing 11.

A controller 16 is also carried by the housing and coupled to the wireless transceiver 12 and the display 13 to perform at least one mobile wireless communications function. For example, the wireless transceiver 12 may be a cellular transceiver or a WiFi transceiver, for example, and may cooperate with the controller 16 and the display 13 to communicate data and/or voice communications. Other types of wireless transceivers and mobile wireless communications functions will be appreciated by those skilled in the art.

The mobile wireless communications device 10 includes one or more input devices 21. The input devices 21 illustratively include push buttons for cooperating with the controller 16 to selectively enable the stabilization mode or set the threshold. In some example embodiments, the input device 21 may be an alphanumeric keypad or other input device for cooperating with the controller 16 to selectively enable the stabilization mode or set a threshold 22, for example. Still further, an input device 21 may be coupled to the display 13 to accept a touching input therefrom and cooperate with the controller 16 to selectively enable the stabilization mode or set a threshold 22, for example.

The orientation sensor 15 is illustratively coupled to the controller 16 and provides orientation information to the controller. The orientation sensor 15 may be an accelerometer, for example. Other orientation sensors that provide orientation information may be used, as will be appreciated by those skilled in the art.

The mobile wireless communications device 10 illustratively includes a memory 17, for example, an on-board/on-chip memory or a removable memory card or both. As will be appreciated by those skilled in the art, the memory 17 may store data relating to the relative orientation and the threshold 22, for example. The memory 17 may also store computer executable code for being executed by the controller 16. In some example embodiments, the computer executable code may be written in Java, for example. Additionally, the computer executable code may be stored on other storage mediums, as will be appreciated by those skilled in the art.

The non-visual indicator 14 may be an internal vibrating device, not shown, and/or an audible indicator, such as an audio transducer 19 that is activated by the controller 16 when the orientation sensor 15 senses a relative angular movement $\alpha$ beyond the threshold 22. The audio transducer may produce an audible beep, alarm, or voice, for example. Other non-visual indicators will be appreciated by those skilled in the art.

The controller 16 is illustratively switchable to stabilization mode. To switch to the stabilization mode, a menu is provided on the display 13 (FIG. 2). The menu items are selected using the buttons 21, or alternatively selected by using a display 13, which may be responsive to touch. Selecting the stabilization mode "on" in the menu switches the controller 16 to the stabilization mode.

If the stabilization mode is enabled, stabilization mode parameters may be set as illustrated by the user 24 (FIG. 3). One mode parameter is the threshold 22. Illustratively, the threshold 22 is a relative angular movement $\alpha$ threshold. The threshold 22 may be measured in degrees and may be set and stored in the memory 17. The threshold 22 may not have to be set by a user, for example, as a default threshold may be already preset or programmed in the memory 17. For example, in some example embodiments the threshold may be set to be less than or equal to 15 degrees from vertical to correspond to a threshold 22 of a relative angular movement $\alpha$ before the user 24 may fall down. More particularly, the threshold may be set to 12.5 degrees, (FIG. 3) for example, which may be helpful to alert the user 24 of an impending fall.

Figures 5A, 5B:
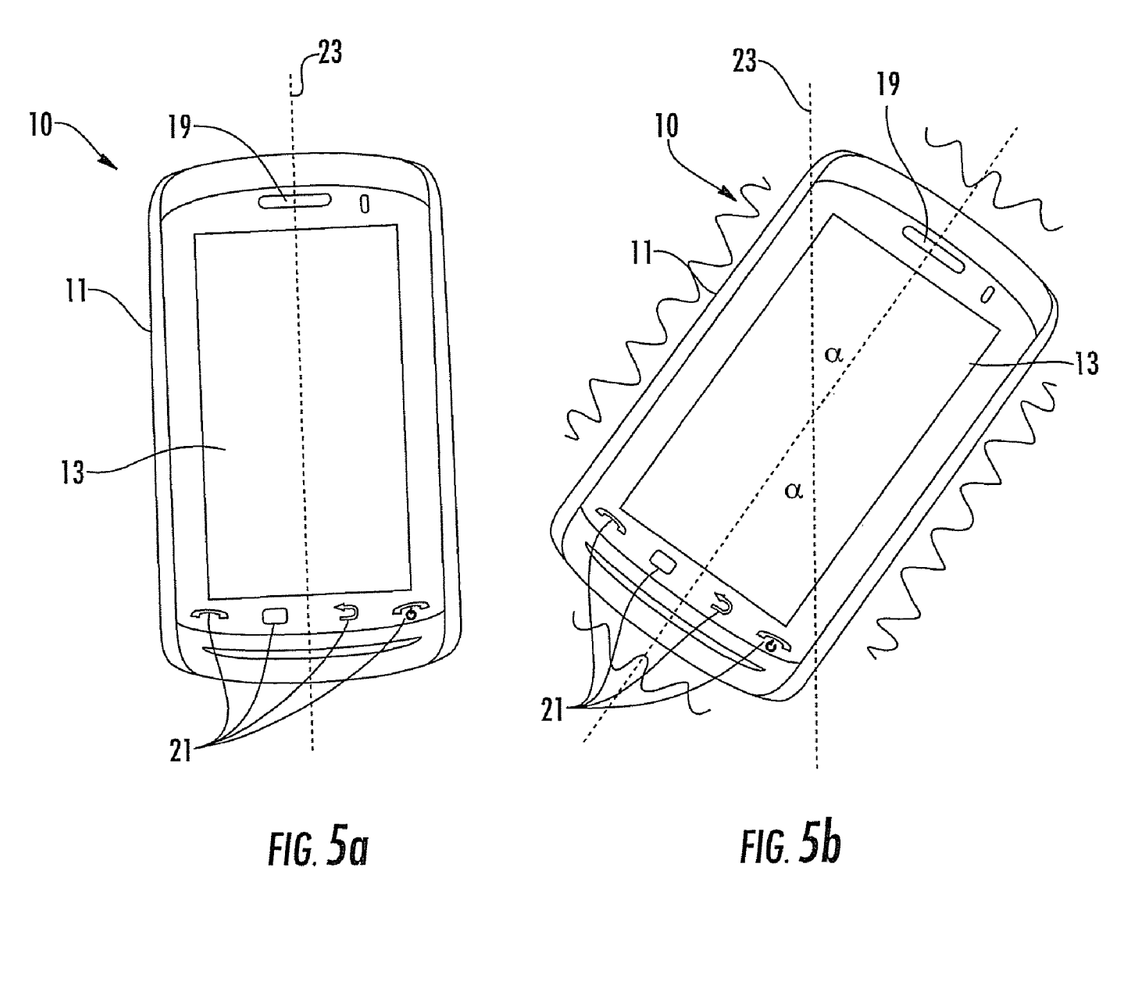
FIGS. 5a-5b are respective plan views of the mobile wireless communications device of FIGS. 1a-1b, according to an example embodiment.
Figure 6A:
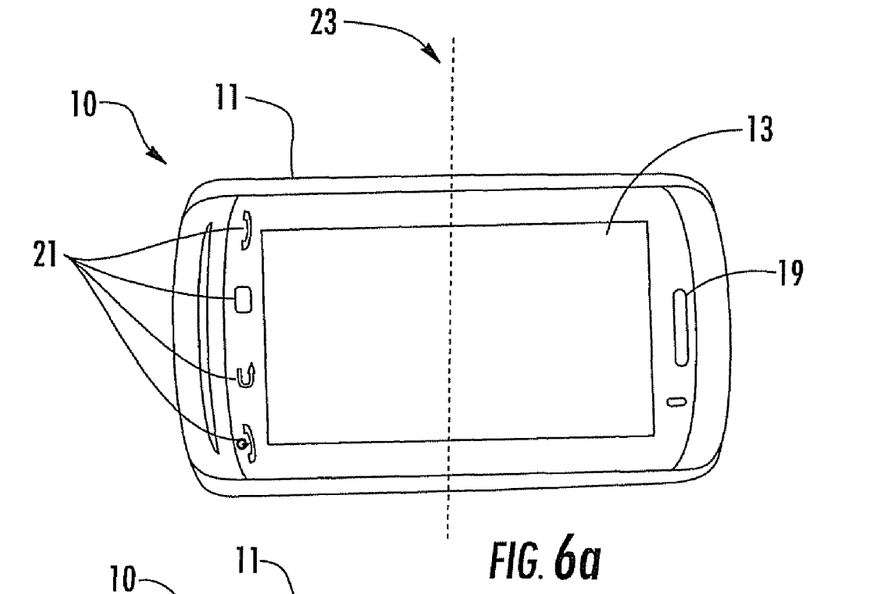
FIGS. 6a-6b are respective plan views of the mobile wireless communications device of FIGS. 1a-1b, in a different configuration, according to an example embodiment.
Figure 6B:
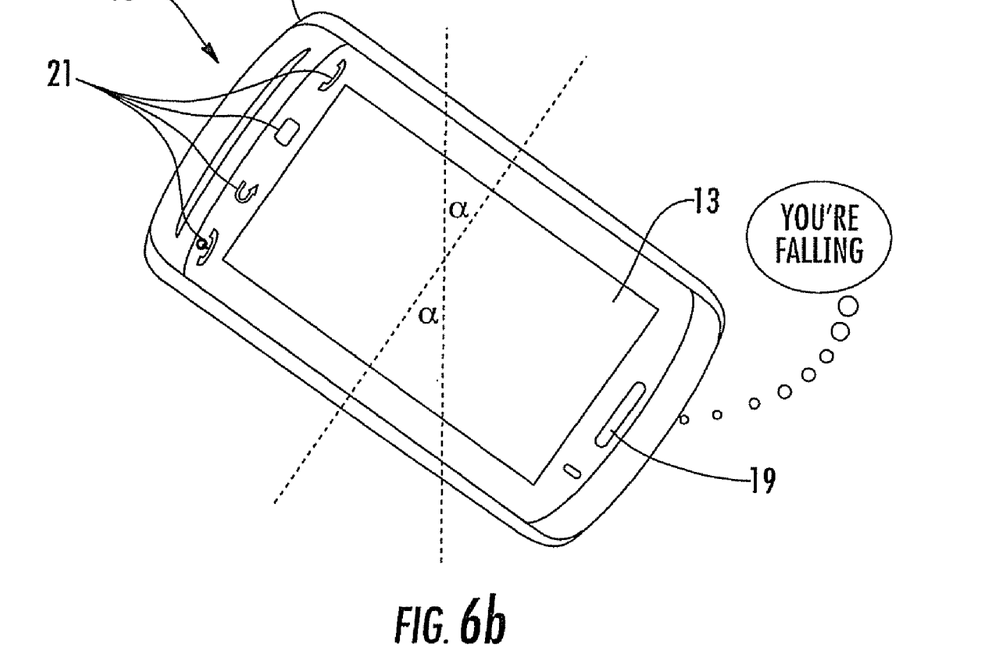

Referring now additionally to FIGS. 5a-5b, an initial reference orientation 23 may also be set from which the relative angular movement $\alpha$ may be sensed. For example, if the mobile wireless communications device 10 is initialized in a vertically oriented position, the relative angular movement $\alpha$ is sensed from the set initial vertical reference orientation 23. As illustrated additionally in FIGS. 6a-6b, if the mobile wireless communications device 10 is initialized in a horizontally oriented position, the relative angular movement $\alpha$ is sensed from the set initial horizontal reference orientation 23. Of course, any orientation of the mobile wireless communications device 10 may be set as the initial reference orientation 23, and the relative angular movement $\alpha$ will be sensed based upon that initial reference orientation, as will be appreciated by those skilled in the art.

As noted above, the non-visual indicator 14 may be a vibratory indicator or an audible indicator, such as an audio transducer. In some example embodiments, the mobile wireless communications device 10 may include more than one non-visual indicator 14, for example, both a vibratory indicator, and an audio transducer. The vibratory indicator may be set to pulse or provide a constant vibration. Similarly, the audio transducer may be set to output a selectable tone or voice message. In the case where more than one non-visual indicator 14 is included in the mobile wireless communications device 10, each non-visual indicator may be selectable to be activated.

Advantageously, the controller 16, when switched to the stabilization mode, cooperates with the orientation sensor 15 to sense a relative angular movement α based upon the initial reference orientation. When relative orientation, as sensed by the orientation sensor 15, exceeds the threshold 22, the controller 16 activates the non-visual indicator 14 as an alert that the threshold 22 has been exceeded. As will be appreciated by those skilled in the art, the threshold 22 may be exceeded in any direction. For example, when the user 24 wears the device 10 in a holster 26 and/or on a belt 25, the non-visual indicator 14 may be activated when the user falls past the threshold 22 in a forward, backward, or sideways direction. Alerting the user 24, for example, a user with a TBI, via the non-visual indicator 14, may reduce a number of falls by alerting the user that they are beginning a fall, for example, when their body exceeds a threshold 22 of less than or equal to 15 degrees, and more particularly, 12.5 degrees relative to vertical. In other words, the user may be alerted before falling or swaying past the point or angle of recovery.

In some example embodiments, for example, a second threshold may be set. For example the controller 16 may activate a second non-visual indicator (not shown) based upon the orientation sensor 15 sensing a relative angular movement α beyond the second threshold. For example, the mobile wireless communications device 10 may vibrate, as a warning, when the second threshold has been exceeded, and provide an audible alarm when the first threshold is exceeded. In other example embodiments, the second threshold may activate the non-visual indicator 14' at a lesser intensity, which increased in intensity as the first threshold is approached. The mobile wireless communications device 10 may also increase vibration or audible alarm intensity after the second threshold is exceeded and reach full intensity at the first threshold. Other threshold and non-visual indicator arrangements will be appreciated by those skilled in the art.

Another aspect is directed to a method of upgrading a mobile wireless communications device 10 that includes a housing 11, a wireless transceiver 12 carried by the housing, a display 13 carried by the housing, a non-visual indicator 14 carried by the housing, and an orientation sensor 15 carried by the housing. A controller 16 is also carried by the housing 11 and coupled to the wireless transceiver 12 and the display 13 to perform at least one communications function. The method includes configuring the controller 16 to be switchable to a stabilization mode to activate the non-visual indicator 14 based upon the orientation sensor 15 sensing relative angular movement α beyond a threshold 22 to thereby upgrade the mobile wireless communications device 10.

Configuring the controller 16 may include accessing stored computer executable code from the memory 17, such as a Java application program interface (API), for example, by using one or more of the input devices 21. Of course, as will be appreciated by those skilled in the art, configuring the controller 16 may occur by the installation of the computer executable code into the memory 17. For example, the controller 16 may be configured by downloading the computer executable code from a third party, or the manufacturer. The controller 16 may also be configured by receiving pushed computer executable code from the third party or the manufacturer.

Using one or more of the input devices 21 configures the controller 16 to switch to the stabilization mode. Once the stabilization mode is enabled, the controller 16 may further be configured by the user 24 to set stabilization mode parameters. For example, the threshold 22, the corresponding type of non-visual indicator 14, and an initial reference orientation 23 may be set. The stabilization mode parameters may not have to be set by the user 24 as they may be already preset or programmed in the memory 17 as default values, for example, by the manufacturer or a third party, or packaged with the computer executable code prior to being pushed or downloaded. Enabling the stabilization mode to be switched on, and setting the stabilization mode parameters advantageously configures the controller 16 to cooperate with the orientation sensor 15 to activate the non-visual indicator 14 based upon sensing the relative angular movement α beyond the threshold 22.

Exemplary components of a hand-held mobile wireless communications device 1000 that may be used in accordance with the present disclosure are further described in the example below with reference to FIG. 7. The device 1000 illustratively includes a housing 1200, a keypad 1400 and an output device 1600. The output device shown is a display 1600, which may comprise a full graphic LCD. In some example embodiments, display 1600 may comprise a touch-sensitive input and output device. Other types of output devices may alternatively be utilized. A processing device 1800 is contained within the housing 1200 and is coupled between the keypad 1400 and the display 1600. The processing device 1800 controls the operation of the display 1600, as well as the overall operation of the mobile device 1000, in response to actuation of keys on the keypad 1400 by the user. In some example embodiments, keypad 1400 may comprise a physical keypad or a virtual keypad (e.g., using a touch-sensitive interface) or both.

The housing 1200 may be elongated vertically, or may take on other sizes and shapes (including clamshell housing structures). The keypad 1400 may include a mode selection key, or other hardware or software for switching between text entry and telephony entry.

Figure 7:
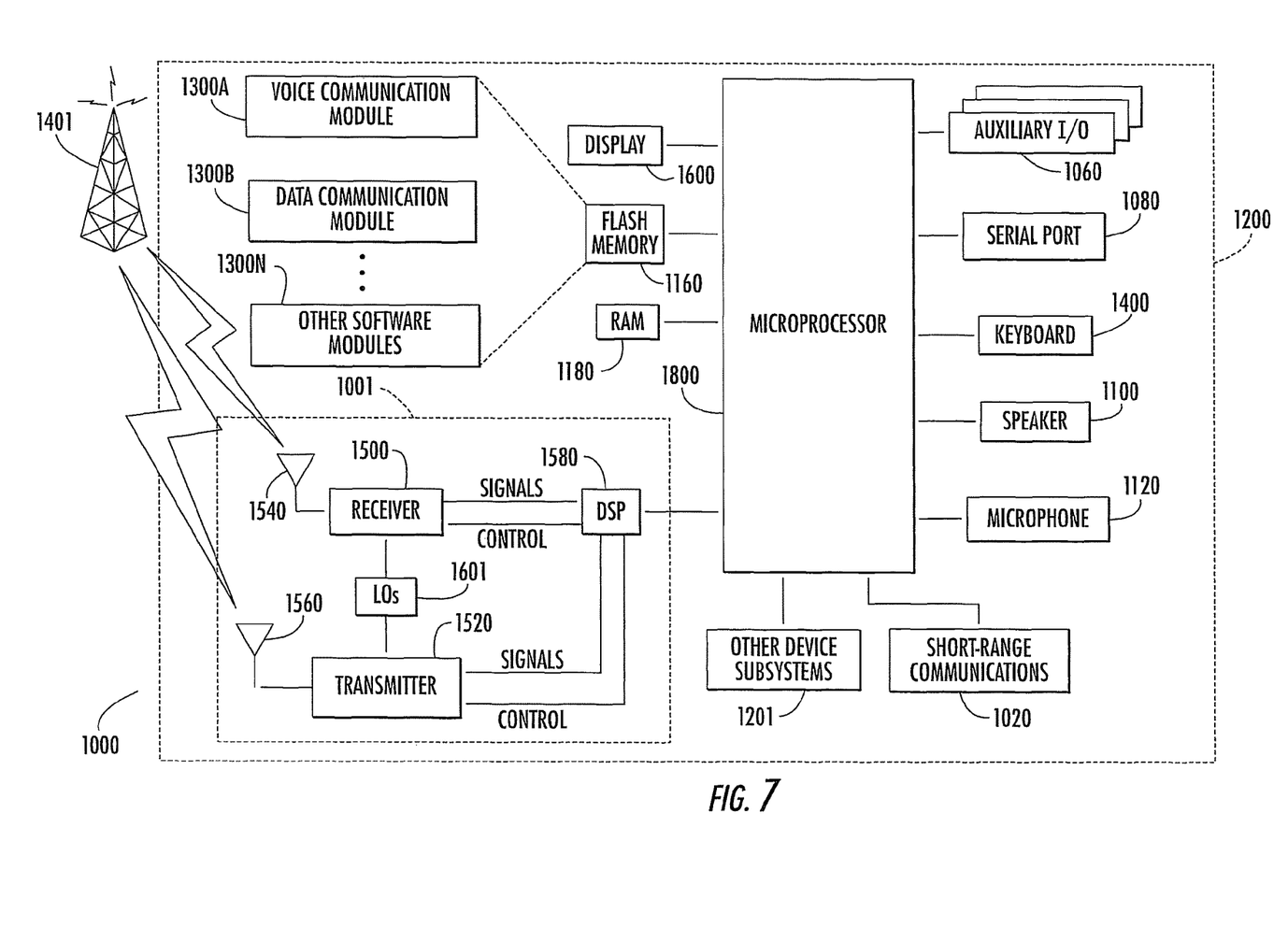
FIG. 7 is a schematic block diagram illustrating exemplary components of a mobile wireless communications device that may be used in accordance with an example embodiment of the present disclosure.

In addition to the processing device 1800, other parts of the mobile device 1000 are shown schematically in FIG. 7. These include a communications subsystem 1001; a short-range communications subsystem 1020; the keypad 1400 and the display 1600, along with other input/output devices 1060, 1080, 1100 and 1120; as well as memory devices 1160, 1180 and various other device subsystems 1201. The mobile device 1000 may comprise a two-way RF communications device having voice and data communications capabilities. In addition, the mobile device 1000 may have the capability to communicate with other computer systems via the Internet.

Operating system software executed by the processing device 1800 may be stored in a persistent store, such as the flash memory 1160, but may be stored in other types of memory devices, such as a read only memory (ROM) or similar storage element in addition, system software, specific device applications, or parts thereof, may be temporarily loaded into a volatile store, such as the random access memory (RAM) 1180. Communications signals received by the mobile device may also be stored in the RAM 1180.

The processing device 1800, in addition to its operating system functions, enables execution of software applications 1300A-1300N on the device 1000. A predetermined set of applications that control basic device operations, such as data and voice communications 1300A and 1300B, may be installed on the device 1000 during manufacture. In addition, a personal information manager (PIM) application may be installed during manufacture. The PIM may be capable of organizing and managing data items, such as e-mail, calendar events, voice mails, appointments, and task items. The PIM application may also be capable of sending and receiving data items via a wireless network 1401. The PIM data items may be seamlessly integrated, synchronized and updated via the wireless network 1401 with the device user's corresponding data items stored or associated with a host computer system.

Communication functions, including data and voice communications, are performed through the communications subsystem 1001, and possibly through the short-range communications subsystem. The communications subsystem 1001 includes a receiver 1500, a transmitter 1520, and one or more antennas 1540 and 1560. In addition, the communications subsystem 1001 also includes a processing module, such as a digital signal processor (DSP) 1580, and local oscillators (LOs) 1601. The specific design and implementation of the communications subsystem 1001 is dependent upon the communications network in which the mobile device 1000 is intended to operate. For example, a mobile device 1000 may include a communications subsystem 1001 designed to operate with the Mobitex™, Data TAC™ or General Packet Radio Service (GPRS) mobile data communications networks, and also designed to operate with any of a variety of voice communications networks, such as AMPS, TDMA, CDMA, WCDMA, PCS, GSM, EDGE, etc. Other types of data and voice networks, both separate and integrated, may also be utilized with the mobile device 1000. The mobile device 1000 may also be compliant with other communications standards such as 3GSM, 3G, UMTS, 4G, etc.

Network access requirements vary depending upon the type of communication system. For example, in the Mobitex and DataTAC networks, mobile devices are registered on the network using a unique personal identification number or PIN associated with each device. In GPRS networks, however, network access is associated with a subscriber or user of a device. A GPRS device therefore utilizes a subscriber identity module, commonly referred to as a SIM card, in order to operate on a GPRS network.

When required network registration or activation procedures have been completed, the mobile device 1000 may send and receive communications signals over the communication network 1401. Signals received from the communications network 1401 by the antenna 1540 are routed to the receiver 1500, which provides for signal amplification, frequency down conversion, filtering, channel selection, etc., and may also provide analog to digital conversion. Analog-to-digital conversion of the received signal allows the DSP 1580 to perform more complex communications functions, such as demodulation and decoding. In a similar manner, signals to be transmitted to the network 1401 are processed (e.g. modulated and encoded) by the DSP 1580 and are then provided to the transmitter 1520 for digital to analog conversion, frequency up conversion, filtering, amplification and transmission to the communication network 1401 (or networks) via the antenna 1560.

In addition to processing communications signals, the DSP 1580 provides for control of the receiver 1500 and the transmitter 1520. For example, gains applied to communications signals in the receiver 1500 and transmitter 1520 may be adaptively controlled through automatic gain control algorithms implemented in the DSP 1580.

In a data communications mode, a received signal, such as a text message or web page download, is processed by the communications subsystem 1001 and is input to the processing device 1800. The received signal is then further processed by the processing device 1800 for an output to the display 1600, or alternatively to some other auxiliary I/O device 1060. A device user may also compose data items, such as e-mail messages, using the keypad 1400 and/or some other auxiliary I/O device 1060, such as a touchpad, a rocker switch, a thumb-wheel, track ball, or some other type of input device. The composed data items may then be transmitted over the communications network 1401 via the communications subsystem 1001.

In a voice communications mode, overall operation of the device is substantially similar to the data communications mode, except that received signals are output to a speaker 1100, and signals for transmission are generated by a microphone 1120. Alternative voice or audio I/O subsystems, such as a voice message recording subsystem, may also be implemented on the device 1000. In addition, the display 1600 may also be utilized in voice communications mode, for example to display the identity of a calling party, the duration of a voice call, or other voice call related information.

The short-range communications subsystem enables communication between the mobile device 1000 and other proximate systems or devices, which need not necessarily be similar devices. For example, the short-range communications subsystem may include an infrared device and associated circuits and components, or a Bluetooth™ communications module to provide for communication with similarly-enabled systems and devices.

Many modifications and other example embodiments of the present disclose will come to the mind of one skilled in the art having the benefit of the teachings presented in the foregoing descriptions and the associated drawings. Therefore, it is understood that the present disclosure is not to be limited to the specific example embodiments disclosed, and that modifications and example embodiments are intended to be included within the scope of the appended claims.

That which is claimed is:

1. A mobile wireless communications device comprising:
    a non-visual indicator;
    an input device;
    an orientation sensor; and
    a controller coupled to the non-visual indicator, the input device, and the orientation sensor, and configured to
        perform at least one mobile wireless communications function, including a voice communication,
        switch to a stabilization mode to activate the non-visual indicator in response to the orientation sensor sensing relative angular movement, relative to a baseline orientation, and beyond a threshold, to alert of an impending fall, and
        cooperate with the input device to set the baseline orientation and the threshold.

2. The mobile wireless communications device according to claim 1 wherein the input device is configured to cooperate with the controller to switch the controller to the stabilization mode.

3. The mobile wireless communications device according to claim 1 wherein the threshold is less than or equal to 15 degrees from vertical.

4. The mobile wireless communications device according to claim 1 wherein the non-visual indicator comprises a vibratory indicator.

5. The mobile wireless communications device according to claim 1 wherein the non-visual indicator comprises an audible indicator.

6. The mobile wireless communications device according to claim 1 wherein the orientation sensor comprises an accelerometer.

7. The mobile wireless communications device according to claim 1 further comprising a memory coupled to the controller for storing the threshold.

8. A mobile wireless communications device comprising:
    a non-visual indicator;

an accelerometer;

an input device; and a controller coupled to the non-visual indicator, the input device, the accelerometer, and the input device, and configured to perform at least one mobile wireless communications function including a voice communication, switch to a stabilization mode based upon the input device to activate the non-visual indicator in response to the accelerometer sensing relative angular movement, relative to a baseline orientation, and beyond the stored threshold, to alert of an impending fall, and cooperate with the input device to set the baseline orientation and the threshold.

9. The mobile wireless communications device according to claim 8 wherein the threshold is less than or equal to 15 degrees from vertical.

10. The mobile wireless communications device according to claim 8 wherein the non-visual indicator comprises at least one of a vibratory indicator and an audible indicator.

11. A method of upgrading a mobile wireless communications device comprising a non-visual indicator, an input device, an orientation sensor, and a controller coupled to the non-visual indicator, the input device and the orientation sensor, the controller being configured to perform at least one communications function, the method comprising:

configuring the controller to be switchable to a stabilization mode to activate the non-visual indicator in response to the orientation sensor sensing relative angular movement, relative to a baseline orientation, and beyond a threshold, to alert a user of an impending fall and thereby upgrade the mobile wireless communications device;

using the input device to set the baseline orientation and the threshold.

12. The method according to claim 11 further comprising using the input device cooperating with the controller to switch the controller to the stabilization mode.

13. The method according to claim 11 wherein the non-visual indicator comprises at least one of a vibratory indicator and an audible indicator.

14. The method according to claim 11 wherein the orientation sensor comprises an accelerometer.

* * * * *

UNITED STATES PATENT AND TRADEMARK OFFICE
CERTIFICATE OF CORRECTION

PATENT NO. : 8,351,894 B2  
APPLICATION NO. : 12/394370  
DATED : January 8, 2013  
INVENTOR(S) : Fields et al.

Page 1 of 1

It is certified that error appears in the above-identified patent and that said Letters Patent is hereby corrected as shown below:

In the Claims

Column 8, Line 44, Claim 1 — Delete: "impending fall, and"  
Insert: --impending fall, [[and]] determine the relative angular movement relative to a base line orientation, and--

Column 9, Line 12, Claim 8 — Delete: "impending fall, and"  
Insert: --impending fall, [[and]] determine the relative angular movement relative to a baseline orientation, and--

Column 10, Line 11, Claim 11 — Delete: "device;"  
Insert: --device, the controller being configured to determine the relative angular movement relative to a baseline orientation; and--

Signed and Sealed this  
Eighteenth Day of June, 2013

Teresa Stanek Rea  
*Acting Director of the United States Patent and Trademark Office*